(12) United States Patent
Bauche et al.

(10) Patent No.: US 8,951,535 B2
(45) Date of Patent: Feb. 10, 2015

(54) LENTIVIRAL VECTORS CONTAINING AN MHC CLASS I PROMOTER

(71) Applicant: Theravectys, Villejuif (FR)

(72) Inventors: Cecile Bauche, Paris (FR); Emeline Sarry, Malakoff (FR)

(73) Assignee: Theravectys, Villejuif (FR)

( * ) Notice: Subject to any disclaimer, the term of this patent is extended or adjusted under 35 U.S.C. 154(b) by 23 days.

(21) Appl. No.: 13/873,922

(22) Filed: Apr. 30, 2013

(65) Prior Publication Data

US 2014/0120132 A1    May 1, 2014

(30) Foreign Application Priority Data

May 23, 2012   (EP) .................................. 12305566

(51) Int. Cl.
| | | |
|---|---|---|
| *C12N 7/01* | (2006.01) | |
| *C12N 15/00* | (2006.01) | |
| *A61K 39/00* | (2006.01) | |
| *C12N 15/86* | (2006.01) | |
| *A61K 39/39* | (2006.01) | |

(52) U.S. Cl.
CPC ............... *C12N 15/86* (2013.01); *C12N 15/00* (2013.01); *A61K 2039/51* (2013.01); *A61K 2039/57* (2013.01); *C12N 2740/15011* (2013.01); *C12N 2740/15041* (2013.01); *A61K 39/00* (2013.01); *C12N 2740/15034* (2013.01); *C12N 2830/008* (2013.01); *A61K 39/39* (2013.01)
USPC ................... 424/199.1; 435/235.1; 435/320.1

(58) Field of Classification Search
None
See application file for complete search history.

(56) References Cited

U.S. PATENT DOCUMENTS

| | | |
|---|---|---|
| 8,093,042 B2 | 1/2012 | Charneau et al. |
| 8,222,029 B2 | 7/2012 | Charneau et al. |
| 8,349,606 B2 | 1/2013 | Charneau et al. |
| 8,367,068 B2 | 2/2013 | Charneau et al. |
| 8,420,104 B2 | 4/2013 | Charneau et al. |
| 2011/0206710 A1 | 8/2011 | Despres et al. |

FOREIGN PATENT DOCUMENTS

| | | | |
|---|---|---|---|
| DE | 19720152 A1 | * | 11/1998 |
| EP | 1092779 A1 | | 4/2001 |
| WO | 2009/019612 A2 | | 2/2009 |

OTHER PUBLICATIONS

Logan et al., Current Opinion in Biotechnology, 2002, 13:429-436.*
Cereb et al., Journal of Immunology, 1994, 152: 3873-3883.*
Breckpot et al., Gene Therapy, 2007, 14:847-862.*
European Patent Office, European Search Report in Appn. EP 12305566.7, Oct. 9, 2012.
Breckpot et al., Lentiviral vectors for cancer immunotherapy: transforming infectious particles into therapeutics, Gene Therapy 14:847-862 (2007).
Chinnasamy, et al., Efficient Gene Transfer to Human Peripheral Blood Monocyte-Derived Dendritic Cells Using Human Immunodeficiency Virus Type 1-Based Lentiviral Vectors, Human Gene Therapy 11:1901-1909 (2000).
Hacien-Bey-Abina et al., Insertional oncogenesis in 4 patients after retrovirus-mediated gene therapy of SCID-XI, Journal of Clinical Investigation 118:3132-3142 (2008).
Yukai et al, Recombinant lentivector as a genetic immunization vehicle for antitumor immunity, Expert Res. Vaccines 6:913-926 (2007).

* cited by examiner

*Primary Examiner* — Nicole Kinsey White
(74) *Attorney, Agent, or Firm* — Law Office of Salvatore Arrigo and Scott Lee, LLP (57) ABSTRACT

The present invention relates to the insertion of a promoter sequence from an MHC class I gene promoter into a lentiviral vector in order to direct the transcription of a transgene, which preferably encodes an immunogenic polypeptide to be expressed in a mammalian cell host, preferably APC (DCs). The invention encompasses these vectors, methods of making the vectors, and methods of using them, including medicinal uses.

19 Claims, 5 Drawing Sheets

SEQUENCE LISTING

```
<160> NUMBER OF SEQ ID NOS: 5

<210> SEQ ID NO 1
<211> LENGTH: 220
<212> TYPE: DNA
<213> ORGANISM: Homo sapiens

<400> SEQUENCE: 1
attggggagt cccagccttg gggattcccc aactccgcag tttcttttct ccctctccca      60
acctatgtag ggtccttctt cctggatact cacgacgcgg acccagttct cactcccatt     120
gggtgtcggg tttccagaga agccaatcag tgtcgtcgcg gtcgcggttc taaagtccgc     180
acgcacccac cgggactcag attctcccca gacgccgagg                            220

<210> SEQ ID NO 2
<211> LENGTH: 197
<212> TYPE: DNA
<213> ORGANISM: Homo sapiens

<400> SEQUENCE: 2
ggggaggcgc agcgttgggg attccccact cccctgagtt tcacttcttc tcccaacttg      60
tgtcgggtcc ttcttccagg atactcgtga cgcgtcccca cttcccactc ccattgggta     120
ttggatatct agagaagcca atcagcgtcg ccgcggtccc agttctaaag tccccacgca     180
cccacccgga ctcagag                                                    197

<210> SEQ ID NO 3
<211> LENGTH: 216
<212> TYPE: DNA
<213> ORGANISM: Homo sapiens

<400> SEQUENCE: 3
cactggggag gcgccgcgtt gaggattctc cactcccctc agtttcactt cttctcccaa      60
cctgcgtcgg gtccttcttc ctgaatactc atgacgcgtc cccaattccc actcccattg     120
ggtgtcgggt tctagagaag ccaatcagcg tctccgcagt cccggtctaa agtccccagt     180
cacccacccg gactcagatt ctccccagac gccgag                               216

<210> SEQ ID NO 4
<211> LENGTH: 205
<212> TYPE: DNA
<213> ORGANISM: Homo sapiens

<400> SEQUENCE: 4
taagaactgc tgattgctgg gaaactctgc agtttcccgt tcctctcgta acctggtcat      60
gtgtccttct tcctggatac tcatgacgca gactcagttc tcattcccaa tgggtgtcgg     120
gtttctagag aagccaatca gcgtcgccac gactcccgac tataaagtcc ccatccggac     180
tcaagaagtt ctcaggactc agagg                                           205

<210> SEQ ID NO 5
<211> LENGTH: 252
<212> TYPE: DNA
<213> ORGANISM: Homo sapiens
```

```
<400> SEQUENCE: 5
aggccccgag gcggtgtctg gggttggaag gctcagtatt gagaattccc catctcccca        60
gagtttctct ttctctccca acccgtgtca ggtccttcat cctggatact cataacgcgg       120
ccccatttct cactcccatt gggcgtcgcg tttctagaga agccaatcag tgtcgccgca       180
gttcccaggt tctaaagtcc cacgcacccc gcgggactca tattttccc agacgcggag        240 gttggggtca tg                                                          252
```

LENTIVIRAL VECTORS CONTAINING AN MHC CLASS I PROMOTER

TECHNICAL FIELD

The present invention is in the field of recombinant vaccine technology and relates to improvements of lentiviral vectors, which can be used as therapeutic and prophylactic vaccines. The vectors containing MHC Class I (MHCI) promoters provide improved characteristics over other vectors.

BACKGROUND

Recombinant vaccines have been developed with the progress of recombinant DNA technology, allowing the modification of viral genomes to produce modified viruses. In this manner, it has been possible to introduce genetic sequences into non-pathogenic viruses, so that they encode immunogenic proteins to be expressed in target cells upon infection, in order to develop a specific immune response in their host.

Such vaccines constitute a major advance in vaccine technology (Kutzler et al., Nat Rev Genet, 9(10): 776-788, 2008). In particular, they have the advantage over traditional vaccines of avoiding live (attenuated) virus and eliminating risks associated with the manufacture of inactivated vaccines.

Gene delivery using modified retroviruses (retroviral vectors) was introduced in the early 1980s by Mann et al. (*Cell*, 33(1):153-9, 1983). The most commonly used oncogenic retroviral vectors are based on the Moloney murine leukemia virus (MLV). They have a simple genome from which the polyproteins Gag, Pol and Env are produced and are required in trans for viral replication (Breckpot et al., 2007, *Gene Ther*, 14(11):847-62; He et al. 2007, *Expert Rev vaccines*, 6(6):913-24). Sequences generally required in cis are the long terminal repeats (LTRs) and its vicinity: the inverted repeats (IR or att sites) required for integration, the packaging sequence ψ, the transport RNA-binding site (primer binding site, PBS), and some additional sequences involved in reverse transcription (the repeat R within the LTRs, and the polypurine tracts, PPT, necessary for plus strand initiation). To generate replication-defective retroviral vectors, the gag, pol, and env genes are generally entirely deleted and replaced with an expression cassette.

Retroviral vectors deriving from lentivirus genomes (i.e. lentiviral vectors) have emerged as promising tools for both gene therapy and immunotherapy purposes, because they exhibit several advantages over other viral systems. In particular, lentiviral vectors themselves are not toxic and, unlike other retroviruses, lentiviruses are capable of transducing non-dividing cells, in particular dendritic cells (He et al. 2007, *Expert Rev vaccines*, 6(6):913-24), allowing antigen presentation through the endogenous pathway.

Lentiviruses are linked by similarities in genetic composition, molecular mechanisms of replication and biological interactions with their hosts. They are best known as agents of slow disease syndromes that begin insidiously after prolonged periods of subclinical infection and progress slowly; thus, they are referred to as the "slow" viruses (Narayan et al., 1989, *J Gen Virol*, 70(7):1617-39). They have the same basic organization as all retroviruses but are more complex due to the presence of accessory genes (e.g., vif, vpr, vpu, nef, tat, and rev), which play key roles in lentiviral replication in vivo.

Lentiviruses represent a genus of slow viruses of the Retroviridae family, which includes the human immunodeficiency viruses (HIV), the simian immunodeficiency virus (SIy), the equine infectious encephalitis virus (EIAV), the caprine arthritis encephalitis virus (CAEV), the bovine immunodeficiency virus (BIV) and the feline immunodeficiency virus (FIV). Lentiviruses can persist indefinitely in their hosts and replicate continuously at variable rates during the course of the lifelong infection. Persistent replication of the viruses in their hosts depends on their ability to circumvent host defenses.

The design of recombinant integrative lentiviral vectors is based on the separation of the cis- and trans-acting sequences of the lentivirus. Efficient transduction in non-dividing cells requires the presence of two cis-acting sequences in the lentiviral genome, the central polypurine tract (cPPT) and the central termination sequence (CTS). These lead to the formation of a triple-stranded DNA structure called the central DNA "flap", which maximizes the efficiency of gene import into the nuclei of non-dividing cells, including dendritic cells (DCs) (Zennou et al., 2000, Cell, 101(2) 173-85; Arhel et al., 2007, *EMBO J*, 26(12):3025-37).

Dendritic cells are of primary importance for antigen presentation because they constitute the main class of antigen presenting cells (APCs) whose primary function is to present antigens and initiate an immune response.

To generate an immune response, antigenic proteins must be processed by cells into peptides that are displayed on the cell surface by major histocompatibility complex proteins (MHCs). Circulating APCs present the peptide-MHC complexes to T cells in the draining lymph nodes, where they interact with T cell receptors, and, in conjunction with co-stimulatory signals, activate the T cells.

A variety of studies have shown that inoculation with lentiviral vectors leads to antigen presentation by DCs and strong activation of antigen specific cytotoxic T lymphocytes (CTLs; $CD8^+$ T cells). Therefore, lentiviral vectors have been engineered for the last 10 years for gene transfer and immunotherapy applications.

Lentiviral vectors have been improved in their safety by removal of the LTR U3 sequence, resulting in "self-inactivating" vectors that are entirely devoid of viral promoter and enhancer sequences originally present within the LTRs.

The lentiviral particles, which contain lentiviral vectors, can be produced by recombinant technology upon transient transfection of HEK 293T human cultured cells by different DNA plasmids:

(i) a packaging plasmid, which expresses at least the Gag, Pol Rev, Tat and, in some cases, structural and enzymatic proteins necessary for the packaging of the transfer construct;

(ii) a transfer plasmid, containing an expression cassette and HIV cis-acting factors necessary for packaging, reverse transcription, and integration; and (iii) an envelope-encoding plasmid, in most cases the glycoprotein of vesicular stomatitis virus (VSV.G), a protein that allows the formation of mixed particles (pseudotypes) that can target a wide variety of cells, especially major histocompatibility (MHC) antigen-presenting cells (APCs), including DCs.

This procedure allows obtaining transient production of lentiviral particle vectors by the transfected cells. However, the lentiviral particle vectors may also be continuously produced by cells by stably inserting the packaging genes, the proviral coding DNA, and the envelope gene into the cellular genome. This allows the continuous production of lentiviral particle vectors by the cells without the need for transient transfection. Of course, a combination of these procedures can be used, with some of the DNAs/plasmids integrated into the cellular genome and others provided by transient transfection.

Non-integrative lentiviral vectors are being designed to mitigate the risks of potential oncogenesis linked to insertional mutagenesis events, particularly for vaccination purposes:

In vaccination based on direct injection of antigen-encoding integrative lentiviral vectors, transduced cells expressing the relevant antigen become targets of the elicited immune response and are eliminated within a few days or weeks from the vaccinated organism.

In addition, deletion in the U3 region of the 3' LTR of the viral promoter and enhancer sequences in self-inactivating lentiviral vectors limits the likelihood of endogenous promoter activation. This deletion directly addresses the experiences gained from the SCID-X1 gene therapy trial carried out in 1998-1999, performed with Moloney virus-based retroviral vectors on children suffering from a rare form of X-linked (SCID-X1 gene) severe immunodeficiency disease (Cavazzana-Calvo et al., 2000, *Science.*, 288(5466):669-72). During this trial, four of nine children developed leukemia as a result of the integration of the Moloney-derived retroviral vector at close proximity to the human LM02 proto-oncogene (Hacein-Bey-Abina et al., 2008, *J. Clin. Invest.*, 118(9):3132-3142). It was demonstrated that malignancy was the consequence of the proximity of the viral U3 promoter/enhancer to the LM02 proto-oncogene.

Enhancers are cis-acting sequences, which can act as transcriptional activators at a distance. They have been widely employed in viral derived vectors because they appear to be the most efficient for obtaining transgene strong expression in a variety of cell types, in particular DCs (Chinnasamy, Chinnasamy et al., 2000, Hum Gene Ther 11(13):1901-9; Rouas et al., 2008, *Cancer Gene Ther* 9(9):715-24; Kimura et al., 2007, *Mol Ther* 15(7):1390-9; Gruh et al., 2008, *J Gene Med* 10(1) 21-32). However, given the safety issue of insertional mutagenesis, such transcriptional enhancer sequences should be deleted from the lentiviral vector constructs to abolish the risk of insertional mutagenesis by enhancer proximity effect. This enhancer proximity effect is by far the most frequent mechanism of insertional mutagenesis and is the only effect described in human or animal cases of tumorigenic events after gene transfer.

Thus, there is a need to develop retroviral, particularly lentiviral vectors, which do not include viral enhancers and which allow sufficient expression of transgenes encoding immunogenic peptides, if possible as much expression as that observed when using the CMV promoter.

A recent study has reported on the replacement of viral promoters by DC-specific promoters deriving from major histocompatibility complex class II genes (MHC class II) (Kimura et al., 2007, *Mol Ther* 15(7):1390-9) and dectin-2 genes (Lopes et al., 2008, *J Virol* 82(1):86-95). The dectin-2 gene promoter used in Lopes et al. contains a putative enhancer and an adenoviral conserved sequence (inverted terminal repeats in adenovirus promoter) (Bonkabara et al., 2001, *J. Immunology*, 167:6893-6900). The MHC class II gene promoter used by Kimura et al. does not contain any known enhancer.

Yet, without an enhancer, the MHC class II promoter was found not to provide sufficient transgene expression in DCs. In particular, lentiviral vectors including MHC class II promoters did not provoke an immune reaction in immunocompetent C57BL/6 mice, in contrast to the immune responses observed with CMV promoters/enhancers. Although integration and persistent transgene expression were observed after injection in mice, the lentiviral vectors transcribed through MHC class II promoters failed to stimulate an antigen-specific CD8+ cytotoxic T-lymphocyte response, even after vaccination boost. The authors of these studies therefore concluded that the use of MHC class II promoters was of interest only for applications where persistence of expression is sought as in gene replacement therapy, but not in the context of immunotherapy.

Thus, the MHC class II promoter is not an adequate promoter for lentiviral vectors for induction of an immune response against an antigen. Moreover, the dectin-2 promoter is dendritic cell specific, which does not allow elimination of vectors that are integrated into other non-expressing cell types. Moreover, the dectin-2 promoter appears to contain an enhancer. Thus, the dectin-2 promoter is not a good promoter for lentiviral vectors for safety reasons.

Preferably, in immunotherapy, lentiviral vectors provide effective expression of the transgene that elicits a desired specific immune response. This requires that the expression is at a high level in APCs, such as dendritic cells.

It is also preferable that the cells transduced by the lentiviral vectors are eliminated by the immune response to provide a higher degree of safety. That is, the immune response generated against the transgene can elicit an immune response in the host sufficient to eliminate the cells that are transduced by the lentiviral vectors. The elimination of transduced cells eliminates the persistence of the lentiviral vector in the host, and possible secondary effects of the vector. In order for the transduced cells to be eliminated, expression is required in non-dendritic cells at a level that allows elimination by the immune response.

At the same time, the promoter should maximize immune stimulation through the key cells (i.e., dendritic cells) involved in the activation of naïve and memory T cells, and should minimize the risk of insertional mutagenesis and genotoxicity in stem cells, leading to malignancies. Thus, the promoter should have sufficiently high activity in dendritic and other cells, but not contain an enhancer. Based on these criteria, viral promoters, such as the CMV promoter, are not ideal because of the presence of strong enhancers. These criteria are summarized as follows:

1. high expression in antigen presenting cells, including dendritic cells, to induce maximal immune responses;
2. expression in other transduced cell types sufficient for elimination by the induced immune response; and
3. lack of an enhancer element to avoid insertional effects.

Thus, a need exists in the art for improved vectors. The present invention fulfils these needs in the art.

SUMMARY OF THE INVENTION

The invention encompasses compositions comprising lentiviral vectors and methods of using the vectors. In one embodiment, the invention encompasses a lentiviral vector comprising a transgene sequence encoding an immunogenic polypeptide, wherein the transgene sequence is under the transcriptional control of a MHC class I promoter; wherein the vector induces a greater CTL response in vivo against the encoded immunogenic polypeptide than a vector in which the transgene sequence is under the transcriptional control of a CMV promoter.

Preferably, the MHC class I promoter is an HLA-A2 promoter, an HLA-B7 promoter, an HLA-Cw5 promoter, an HLA-E promoter, or an HLA-F promoter.

In various embodiments, the promoter sequence comprises a polynucleotide sequence that shares more than 90%, preferably more than 95%, more preferably more than 99% identity with the promoter sequence of SEQ ID NO:1, SEQ ID NO:2, SEQ ID NO:3, SEQ ID NO:4, or SEQ ID NO:5.

In various embodiments, the vector comprises an LTR that is deleted for the promoter and enhancer of U3, a cPPT/CTS sequence from a lentivirus, a ψ (psi) sequence, and/or two lentiviral LTRs.

In a preferred embodiment, the lentiviral vector does not contain an enhancer.

The immunogenic polypeptide encoded by the transgene comprises antigen(s) from Gag, Pol and/or Nef proteins from HIV virus. The antigen can be at least one tumour antigen.

The invention further encompasses an isolated host cell comprising the lentiviral vector of the invention.

The invention further encompasses methods for producing a lentiviral vector particle. Such methods can comprise the steps of transfecting a suitable host cell with the lentiviral vector; transfecting the host cell with a packaging plasmid vector containing viral DNA sequences encoding at least structural and integrase proteins of a retrovirus; culturing said transfected host cell in order to obtain expression and packaging of said lentiviral vector into lentiviral vector particles; and harvesting the lentiviral vector particles resulting from the expression and packaging in said cultured host cells.

The invention further encompasses lentiviral vector particles comprising the lentiviral vector of the invention. The lentiviral vector particle can comprise a cPPT/CTS polynucleotide sequence; a LTR that is deleted for the promoter and enhancer of U3; and/or a transgene sequence under control of an MHC class I promoter. Preferably, the promoter sequence comprises a polynucleotide sequence that shares more than 90%, preferably more than 95%, more preferably more than 99% identity with the promoter sequence of SEQ ID NO. 1, SEQ ID NO:2, SEQ ID NO:3, SEQ ID NO:4, or SEQ ID NO:5.

The invention further encompasses compositions comprising a lentiviral vector or lentiviral vector particle according to the invention for use as a medicament or vaccine.

The invention further encompasses methods for inducing a T-cell response comprising administering to a patient a lentiviral vector particle comprising a cPPT/CTS polynucleotide sequence; a LTR that is deleted for the promoter and enhancer of U3; and/or a transgene sequence under control of an MHC Class I promoter.

BRIEF DESCRIPTION OF THE DRAWINGS

The MHC Class I (MHCI) promoters show conserved regulatory elements: κB (NF-κB binding site), ISRE (Interferon stimulated response element), SXY (SXY regulatory elements), TATA (transcriptional signal) and ATG (start codon for the transgene traduction). The MHCII promoter family only shows the SXY, TATA and ATG regulatory elements.

Lentivector constructions having various promoters linked to a green fluorescent protein (GFP) gene were used to transduce HEK293T and BDCM cells, and the promoters' ability to drive the GFP expression was evaluated FIGS. 3A and B. Induction of GFP expression by various Interferons Lentivectors having various promoters were used to transduce HEK293T and BDCM cells in presence of various interferon molecules. The promoters' ability to drive the GFP expression was then evaluated. MFI in 293T (A) and in BDCM cells (B) is shown. Reduced versions of the MHCI and β2m promoters were also tested, promoters in which the κB and ISRE regulatory sequences were removed, transforming them into an MHCII-like promoters.

C57Bl/6j mice were immunized with $1.10^6$ TU of lentivectors in which HIV antigen expression is driven by the indicated promoters. 12 days after immunization, the specific T-cell responses against the HIV antigen were monitored in mice splenocytes by IFN-γ ELISPOT.

DETAILED DESCRIPTION OF THE INVENTION

In order to determine if promoters existed that might meet the criteria of high expression in dendritic cells to induce maximal immune responses; expression in other transduced cell types sufficient for elimination by the induced immune response; and lack of an enhancer element to avoid insertional effects, human gene promoters were investigated for their utility in lentiviral vectors. Human promoters were analyzed for their expression levels in dendritic cells and in other tissues. Promoters with expected high levels of dendritic cell expression and relatively high mean expression in all tissues were selected using a quantitative analysis. The promoters were further selected for lack of enhancer sequences.

Figure 1:
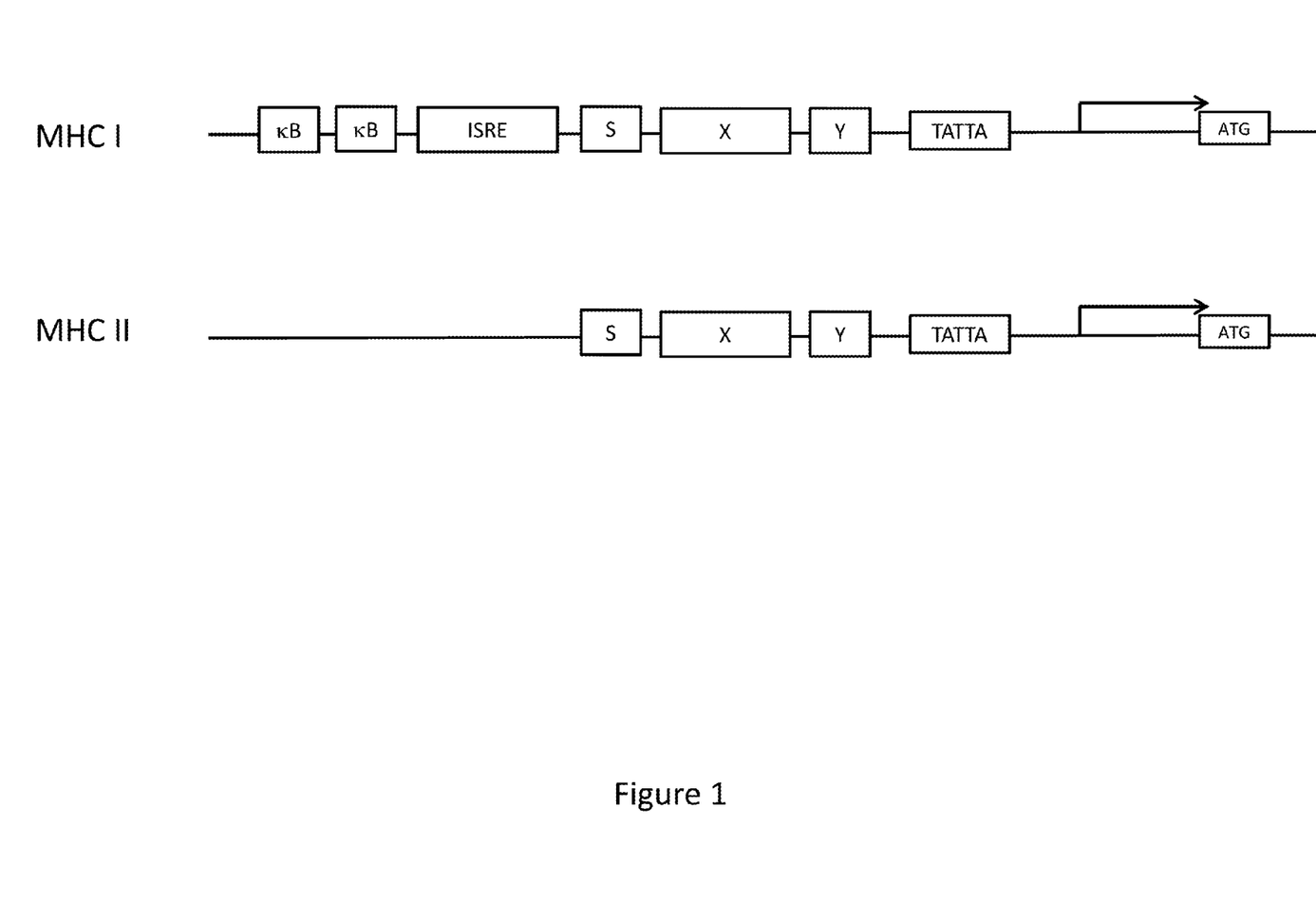
FIG. 1. Schematic representation of the MHCI and MHCII promoters

One group of promoters that meets these criteria is MHC Class I promoters. MHC Class I promoters show conservation of NF-Kb binding sites, an interferon stimulated response element (ISRE), and an SXY regulatory module (SXY). The arrangement of these elements in MHC Class I promoters is depicted in FIG. 1.

MHC Class II promoters are considered to be antigen presenting cell (including dendritic cell)-specific promoters. As can also be seen in FIG. 1, although MHC class II promoters contain an SXY module, they do not contain NF-Kb binding sites or an ISRE (Van den Nelsen et al, 1998, *Immunogenetics*, 48:208-221). Thus, MHC Class II promoters are quite different from MHC Class I promoters.

Another antigen presenting cell-specific promoter, dectin-2, contains an interferon stimulated response element (ISRE); but does not contain an SXY module (Bonkabara et al., 2001, *J. Immunology*, 167:6893-6900).

The human β2-microglobulin (β2m) promoter shows some similarity to the MHC Class I promoters, as it contains an ISRE, albeit upstream of a single NF-Kb binding site.

The sequences of various mammalian (human) MHC class I promoters are shown below:

```
HLA-A2 (MHC I):                              (SEQ ID NO: 1)
attggggagtcccagccttggggattccccaactccgcagtttcttttct ccctctcccaacctatgtagggtccttcttcctggatactcacgacgcgg acccagttctcactcccattgggtgtcgggtttccagagaagccaatcag tgtcgtcgcggtcgcggttctaaagtccgcacgcacccaccgggactcag attctcccagacgccgagg HLA-B7 (MHC I):
ggggaggcgcagcgttggggattccccactcccctgagtttcacttcttc tcccaacttgtgtcgggtccttcttccaggatactcgtgacgcgtcccca cttcccactcccattgggtattggatatctagagaagccaatcagcgtcg ccgcggtcccagttctaaagtccccacgcacccaccggactcagag
```

-continued

HLA-Cw5 (MHC I): (SEQ ID NO: 3)
cactggggaggcgccgcgttgaggattctccactccctcagtttcactt cttctcccaacctgcgtcgggtccttcttcctgaatactcatgacgcgtc cccaattcccactcccattgggtgtcgggttctagagaagccaatcagcg tctccgcagtcccggtctaaagtcccagtcacccacccggactcagatt ctccccagacgccgag HLA-E (MHC I): (SEQ ID NO: 4)
taagaactgctgattgctgggaaactctgcagtttcccgttcctctcgta acctggtcatgtgtccttcttcctggatactcatgacgcagactcagttc tcattcccaatgggtgtcgggtttctagagaagccaatcagcgtcgccac gactcccgactataaagtcccatccggactcaagaagttctcaggactc agagg HLA-F (MHC I): (SEQ ID NO: 5)
aggccccgaggcggtgtctggggttggaaggctcagtattgagaattccc catctcccagagtttctctttctctcccaacccgtgtcaggtccttcat cctggatactcataacgcggcccatttctcactcccattgggcgtcgcg tttctagagaagccaatcagtgtcgccgcagttcccaggttctaaagtcc cacgcacccgcgggactcatatttttcccagacgcggaggttggggtca tg MHCI promoters (HLA-A2, HLA-B7 or HLA-E) were inserted into a lentiviral vector. For comparison, the promoters of the ubiquitously expressed EF1α and Ubiquitin (UBC) genes were also inserted into the lentiviral vector. EF1α and Ubiquitin promoters do not contain any identified enhancers, and do not contain an SXY module, NF-Kb binding sites or an ISRE. Rather, the EF1α and Ubiquitin (UBC) promoters instead contain Sp1 and Ap1 binding sites. A vector containing the CMV promoter was also generated. Vectors containing an MHCII promoter (HLA-DRα) or a β2m promoter were also generated. In these vectors, the promoters drive expression of green fluorescent protein (GFP).

To look for dendritic cell-specific expression, the vectors were packaged by cotransfection in HEK 293 T cells with an encapsidation plasmid and a plasmid providing VSV.G envelope, essentially as described in Naldini et al, 1996, *Science* 272:263-7. Both HEK 293 T and BDCM cells (a dendritic-like cell line) were then transduced with of particles of the different vectors. Expression was detected in HEK 293 T cells with all vectors.

Figure 2:
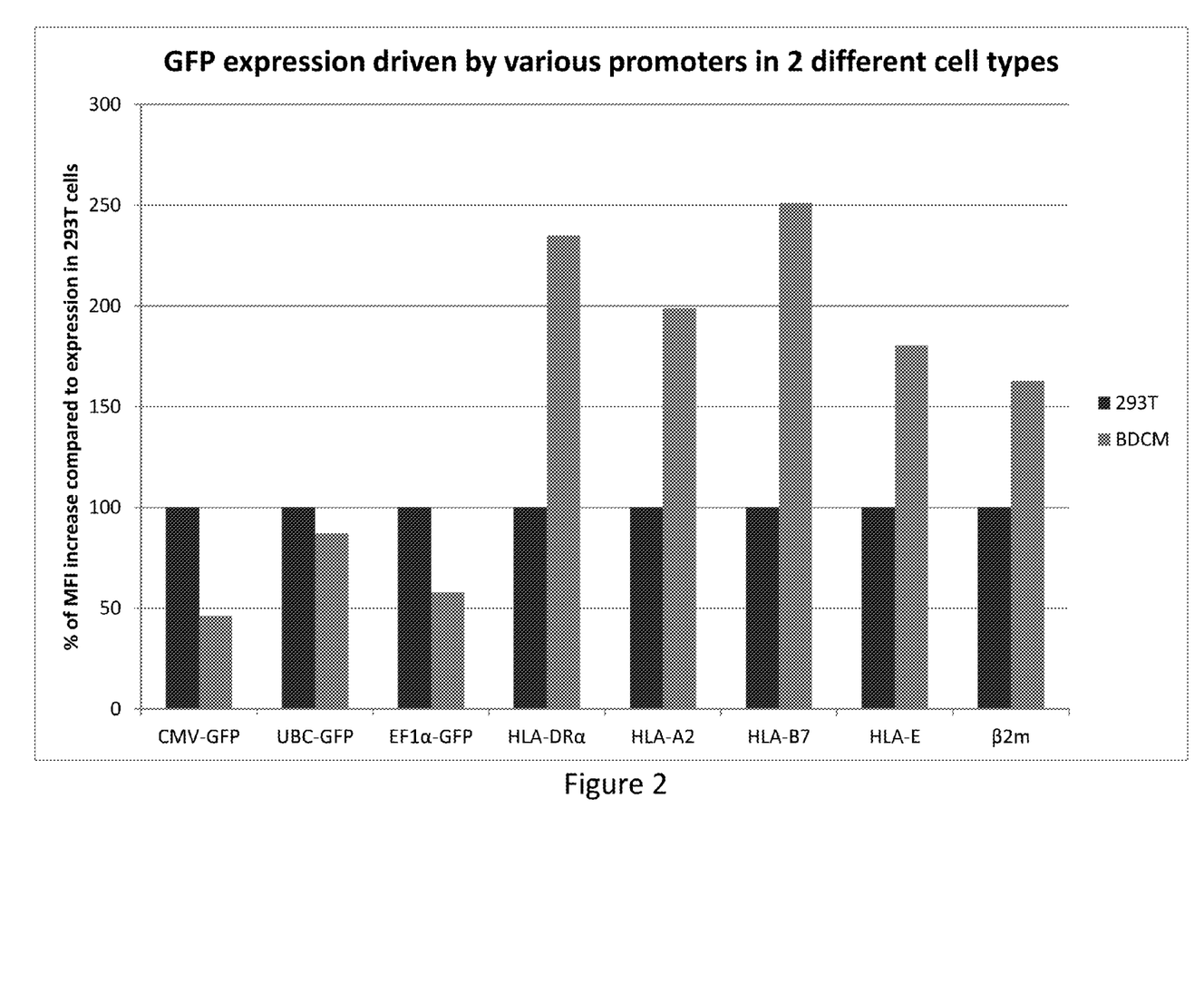
FIG. 2. GFP expression driven by various promoters in two different cell types.

Vectors with a CMV promoter, an UBC promoter, or an EF1α promoter demonstrated higher expression in HEK 293 T cells than in BDCM cells (FIG. 2). However, vectors with an MHCII promoter (HLA-DRα), MHCI promoter (HLA-A2, HLA-B7 or HLA-E), or β2 microglobulin promoter (β2m) showed higher expression in BDCM cells than in HEK 293 T cells. Thus, these promoters all exhibited a dendritic cell-specific overexpression.

Figure 3A:
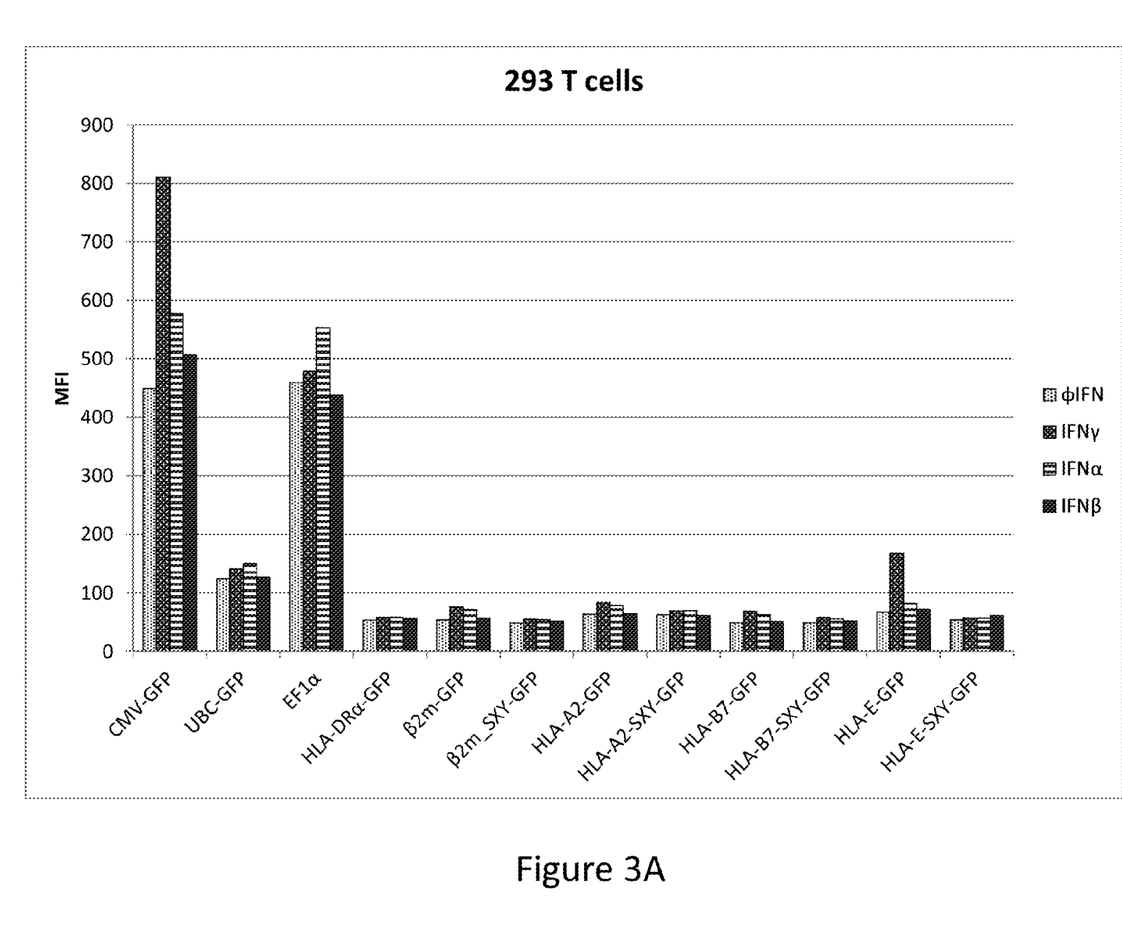
Figure 3B:
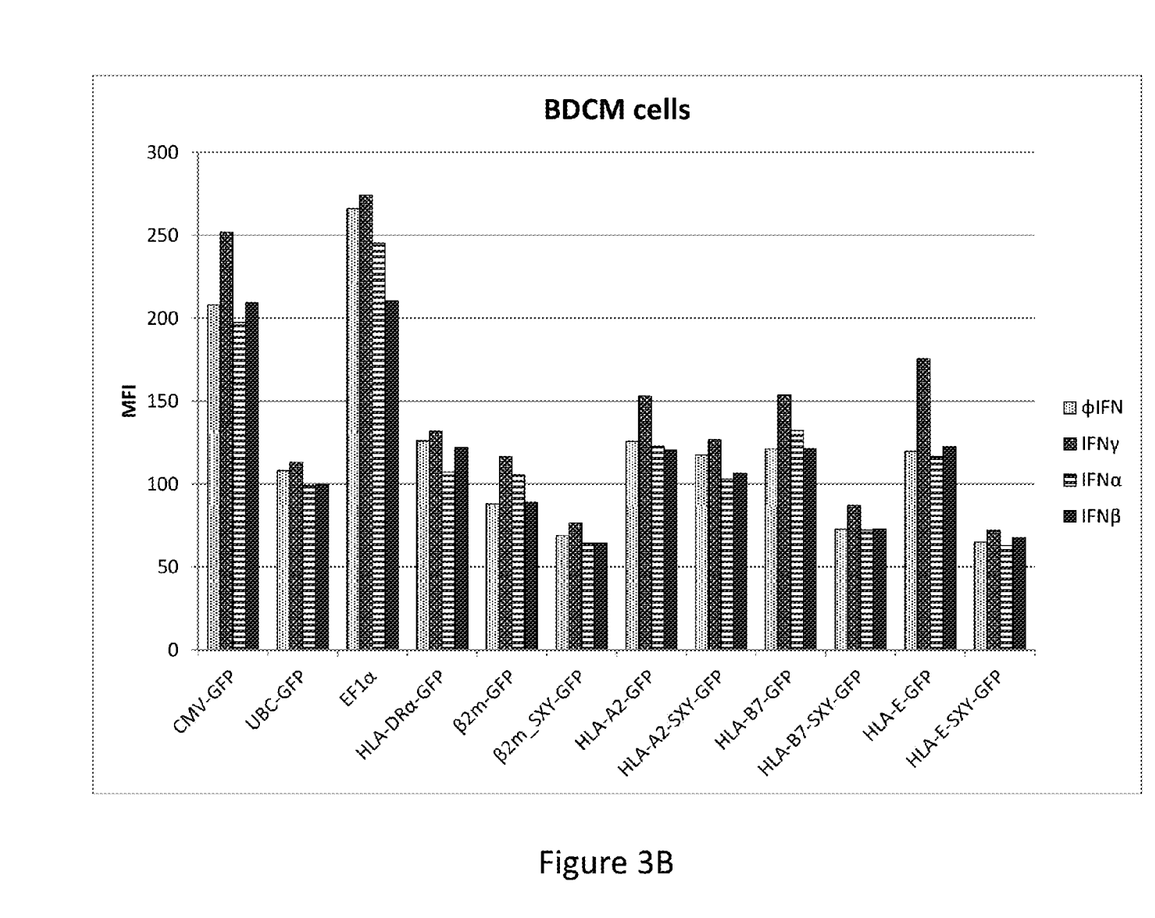

Induction of expression in the presence of various interferons was also assessed. The results are shown in FIGS. 3A and B. The MHCII promoter was not inducible by interferons. However, the MHCI promoters were inducible by interferon γ in both cell types and by interferon α in HEK 293 T cells. Similar to the MHCI promoters, the β2m promoter was also inducible by interferons. Truncation of the MHCI or β2m promoters to remove the ISRE and the NF-Kb binding sites (promoter-SXY-GFP), reduced inducibility. Thus, the truncated version of the HLA-A2, HLA-B7, HLA-E, and β2m promoters behave like a MHCII promoter with respect to inducibility.

Figure 4:
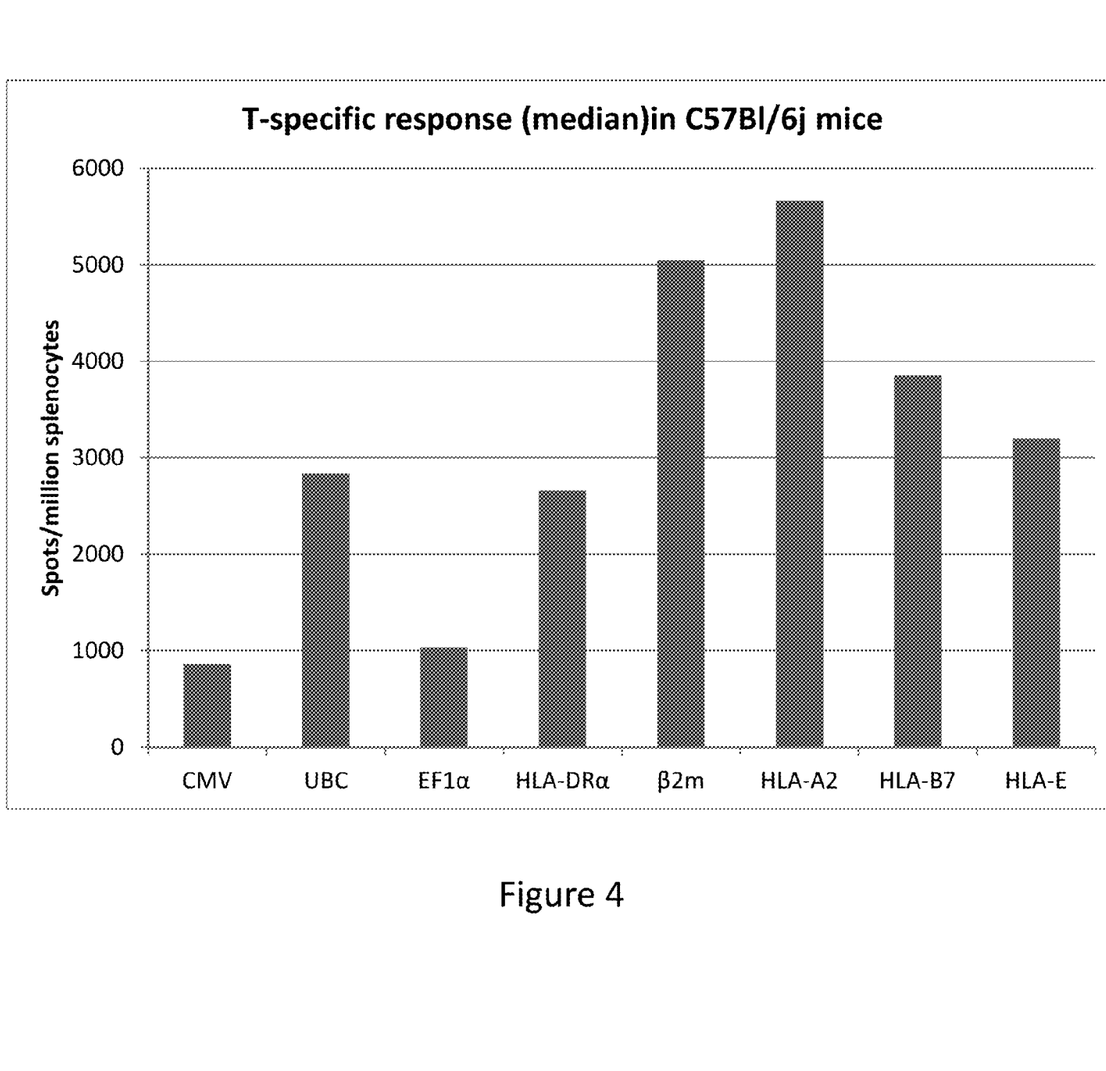
FIG. 4. T-specific response (median) in C57Bl/6j mice

Next, mice were immunized with lentivectors in which HIV antigen expression is driven by various promoters (viral, ubiquitous, MHCI, MHCII, and β2m). 12 days after immunization, the specific T-cell responses were monitored in mice splenocytes by IFN-γ ELISPOT. As shown in FIG. 4, immunization with a lentivector with an MHCI promoter gave the highest specific T-cell response.

As seen in FIG. 4, the T-specific response with the MHCI promoters was higher than with CMV, EF1α, Ubiquitin, or MHCII promoters, and more than 3 fold higher than that with EF1α or CMV promoters. The T-specific response with the β2m promoter was similar to the MHCI promoters. These results indicate that the MHCI promoter is an unexpectedly superior promoter to the EF1α, Ubiquitin, CMV, or MHCII promoters for use in lentivectors for maximizing the T-specific response in vivo.

The present invention encompasses lentiviral vectors comprising MHC class I (MHCI)-containing promoters, and their use for the induction of immune responses in a host.

The present invention has thus, as a main object, a lentiviral vector comprising a promoter sequence from a class I MHC gene promoter that directs the transcription of a transgene, which preferably encodes an immunogenic polypeptide, in a cell of a host, preferably in dendritic cells (DCs).

Lentiviral Vector

Within the context of this invention, a "lentiviral vector" means a non-replicating vector for the transduction of a host cell with a transgene comprising cis-acting lentiviral RNA or DNA sequences, and requiring lentiviral proteins (e.g., Gag, Pol, and/or Env) that are provided in trans. The lentiviral vector lacks expression of functional Gag, Pol, and Env proteins. The lentiviral vector may be present in the form of an RNA or DNA molecule, depending on the stage of production or development of said retroviral vectors.

The lentiviral vector can be in the form of a recombinant DNA molecule, such as a plasmid. The lentiviral vector can be in the form of a lentiviral particle vector, such as an RNA molecule(s) within a complex of lentiviral and other proteins. Typically, lentiviral particle vectors, which correspond to modified or recombinant lentivirus particles, comprise a genome which is composed of two copies of single-stranded RNA. These RNA sequences can be obtained by transcription from a double-stranded DNA sequence inserted into a host cell genome (proviral vector DNA) or can be obtained from the transient expression of plasmid DNA (plasmid vector DNA) in a transformed host cell.

Lentiviral vectors derive from lentiviruses, in particular human immunodeficiency virus (HIV-1 or HIV-2), simian immunodeficiency virus (SIV), equine infectious encephalitis virus (EIAV), caprine arthritis encephalitis virus (CAEV), bovine immunodeficiency virus (BIV) and feline immunodeficiency virus (FIV), which are modified to remove genetic determinants involved in pathogenicity and introduce new determinants useful for obtaining therapeutic effects.

Such vectors are based on the separation of the cis- and trans-acting sequences. In order to generate replication-defective vectors, the trans-acting sequences (e.g., gag, pol, tat, rev, and env genes) can be deleted and replaced by an expression cassette encoding a transgene.

Efficient integration and replication in non-dividing cells generally requires the presence of two cis-acting sequences at the center of the lentiviral genome, the central polypurine tract (cPPT) and the central termination sequence (CTS). These lead to the formation of a triple-stranded DNA structure called the central DNA "flap", which acts as a signal for uncoating of the pre-integration complex at the nuclear pore and efficient importation of the expression cassette into the nucleus of non-dividing cells, such as dendritic cells.

In one embodiment, the invention encompasses a lentiviral vector comprising a central polypurine tract and central termination sequence referred to as cPPT/CTS sequence as described, in particular, in the European patent application EP 2 169 073.

Further sequences are usually present in cis, such as the long terminal repeats (LTRs) that are involved in integration of the vector proviral DNA sequence into a host cell genome. Vectors may be obtained by mutating the LTR sequences, for instance, in domain U3 of said LTR (ΔU3) (Miyoshi H et al, 1998, *J. Virol.* 72(10):8150-7; Zufferey et al., 1998, *J Virol* 72(12):9873-80) as shown in FIG. 1.

Preferably, the vector does not contain an enhancer. In one embodiment, the invention encompasses a lentiviral vector comprising LTR sequences, preferably with a mutated U3 region (ΔU3) removing promoter and enhancer sequences in the 3' LTR.

The packaging sequence ψ (psi) can also be incorporated to help the encapsidation of the polynucleotide sequence into the vector particles (Kessler et al., 2007, *Leukemia*, 21(9): 1859-74; Paschen et al., 2004, *Cancer Immunol Immunother* 12(6):196-203).

In one embodiment, the invention encompasses a lentiviral vector comprising a lentiviral packaging sequence ψ (psi).

Further additional functional sequences, such as a transport RNA-binding site or primer binding site (PBS) or a Woodchuck PostTranscriptional Regulatory Element (WPRE), can also be advantageously included in the lentiviral vector polynucleotide sequence of the present invention, to obtain a more stable expression of the transgene in vivo.

In one embodiment, the invention encompasses a lentiviral vector comprising a PBS. In one embodiment, the invention encompasses a lentiviral vector comprising a WPRE and/or an IRES.

Thus, in a preferred embodiment, the lentiviral vector comprises at least one cPPT/CTS sequence, one ψ sequence, one (preferably 2) LTR sequence, and an expression cassette including a transgene under the transcriptional control of a class I MHC promoter.

In various embodiments, the lentiviral vector comprises an MHC class I promoter. Preferably, the MHC class I promoter is an HLA-A2 promoter, an HLA-B7 promoter, an HLA-Cw5 promoter, an HLA-F or an HLA-E promoter. In various embodiments, the MHC class I promoter sequence comprises a polynucleotide sequence that shares more than 90%, preferably more than 95%, more preferably more than 99% identity with the promoter sequence of SEQ ID NO:1, SEQ ID NO:2, SEQ ID NO:3, SEQ ID NO:4, or SEQ ID NO:5

In various embodiments, the lentiviral vector comprising an MHC class I promoter induces a greater CTL response in vivo against the encoded immunogenic polypeptide than a vector in which the transgene sequence is under the transcriptional control of a CMV promoter.

In various embodiments, the lentiviral vector comprising an MHC class I promoter induces a greater CTL response in vivo against the encoded immunogenic polypeptide than a vector in which the transgene sequence is under the transcriptional control of an EF1α promoter. Preferably, the CTL response with the MHCI promoter is at least 2-fold or 3-fold higher than with the EF1α promoter. Within the context of this invention, whether a vector "induces a greater CTL response in vivo against the encoded immunogenic polypeptide than a vector in which the transgene sequence is under the transcriptional control of an EF1αpromoter" can be determined using the assay set forth in Example 3. Other assays that provide similar results can also be used.

In various embodiments, the lentiviral vector comprising an MHC class I promoter induces a greater CTL response in vivo against the encoded immunogenic polypeptide than a vector in which the transgene sequence is under the transcriptional control of an Ubiquitin promoter. Within the context of this invention, whether a vector "induces a greater CTL response in vivo against the encoded immunogenic polypeptide than a vector in which the transgene sequence is under the transcriptional control of an Ubiquitin promoter" can be determined using the assay set forth in Example 3. Other assays that provide similar results can also be used.

Transgene

Within the context of this invention, a "transgene" is a nucleic acid sequence within a lentiviral vector that is not normally present in a cell to be transduced with the lentiviral vector. The lentiviral vector serves to introduce this sequence into the transduced cell. The term "transgene" does not include those sequences of the vector that facilitate transduction of the transgene. The transgene may be a nucleic acid sequence from another organism. Alternatively, the transgene may be a nucleic acid sequence from the same organism, but having different regulatory sequences controlling its expression. The transgene may be a sense or antisense nucleic acid molecule. According to a preferred embodiment of the invention, the transgene sequence encodes an immunogenic polypeptide.

Preferably, the immunogenic polypeptide is viral, bacterial, or fungal. In one embodiment, the immunogenic polypeptide is a tumor antigen. In one embodiment, the immunogenic polypeptide is an allergen.

This immunogenic polypeptide preferably comprises one or several epitope(s) from agents of infectious diseases, for example antigen(s) from Gag, Pol, and/or Nef proteins of HIV.

Several epitopes forming a polyepitope may also be encoded by the transgene of the invention.

In a particular embodiment, such epitope is derived from target antigens identified in tumors, and can be chosen in such a way that a cell-mediated immune response is obtained against it. Target antigens are well documented in the art, which can be selected with respect to several types of tumors and in particular in melanomas or in carcinomas, including renal carcinomas, bladder carcinomas, colon carcinomas, lung carcinomas, breast cancers, leukemias, myelomas and lymphomas.

MHCI Promoters

The invention encompasses the insertion of an MHC Class I (MHCI) promoter into a lentiviral vector. As used herein, an "MHC Class I (MHCI) promoter" includes a naturally occurring or synthetic MHC Class I promoter. The term "MHC Class I promoter" does not include a β2m promoter.

Naturally Occurring MHCI Promoters

Examples of naturally occurring MHCI promoters are the HLA-A2, HLA-B7, HLA-Cw5, HLA-E, HLA-F gene promoters. These naturally occurring MHCI promoters are generally cloned or reproduced from the promoter region of a gene encoding the MHC class I protein, or referred to as putatively encoding such proteins in genome databases (ex: NCBI polynucleotide database http://www.ncbi.nlm.nih.gov/guide/dna-rna). Both β2m and class I MHC proteins enter the Major Histocompatibility Complex (MHC).

The proteins encoded by these genes are found in almost all cell types. MHCI proteins are generally present at the surface of the membrane of leucocytes, where they are associated with the β2-microglobulin (β2m). The role of these associated proteins is to present peptides from endogenous sources to CD8+ T cells. They thus play a central role to the generation of the antigen-specific immune response. Because MHC class I proteins have been widely studied and described for many years, their genes are well characterized and detectable using sequence comparison tools, such as the BLAST method (Altschul, S. F. et al. (1990). Basic local alignment search tool. *J. Mol. Biol.* 215(3):403-410).

MHC class I promoters share the ability to be strongly activated in antigen presenting cells, including dendritic cells, as well as, to lower intensity, in the majority of the other human body tissues.

The MHC class I promoters of the invention can contain further regulatory elements, such as one or more Sp1 and ETs binding sites. In a preferred embodiment, the MHC class I promoter contains 2 Sp1 binding sites and 1 Ets binding site. In other embodiments, Ap1 and/or Ap2 sites are further contained in the MHC class I promoter.

Preferred promoters are human HLA-A2, HLA-B7, HLA-Cw5, HLA-E and HLA-F promoters.

Synthetic MHC Class I Promoters

MHC class I promoters can also be synthetic. Synthetic MHC class I promoters include promoters that are synthesized using molecular biological techniques to assemble the individual components of an MHC class I promoter or that are derived from naturally occurring MHC class I promoter using molecular biological techniques.

In various embodiments, the synthetic MHC class I promoter comprises a polynucleotide sequence that shares more than 90%, preferably more than 95%, more preferably more than 99% identity with the promoter sequence of a MHC class I gene promoter (SEQ ID NOs: 1-5).

ISRE

The transcription of MHC class genes are usually mediated by two major regulatory elements: Interferon stimulated response element (ISRE) and the SXY module (encompassing the W/S, X1X2/Site α and Y/enhancer B regulatory elements) (see FIG. 1). See also Van den Elsen, Immunogenetics (1998) 48:208-211.

These regulatory promoter elements are localized in a region extending approximately from nucleotides −220 to −95 upstream of the transcription initiation site. They mediate tissue-specific and cytokine-induced transcription of MHC class I genes.

The ISRE of MHC class I gene promoters generally contains binding sites for interferon regulatory factor (IRF) family members. It is thus a property of MHC class I promoters to bind to interferon regulatory factor (IRF) family members. This may be verified, for example, by gel shift assays.

NF-κB Binding Site

Another regulatory element, the enhancer A (containing binding sites for nuclear transcription factor κB (NF-κB)) is present in most cases. It is thus a property of MHC class I promoters to bind to nuclear transcription factor κB (NF-κB). This may be verified, for example, by gel shift assays.

SXY Module

In addition to ISRE, MHC class I promoters generally share another set of conserved upstream sequence motifs, consisting of three regulatory elements: the S or W box, the X1/CREX2 boxes or site α, and the Y box or enhancer B, which together are termed the SXY module. This SXY module is generally cooperatively bound by a multiprotein complex containing regulatory factor X (RFX; consisting of RFX5, RFXB/ANK and RFXAP), cAMP response element binding protein (CREB)/activating transcription factor (ATF), and nuclear factor Y (NFY), which acts as an enhanceosome driving transactivation of these genes. It is thus a property of MHC class I promoters to bind to these factors. This may be verified, for example, by gel shift assays.

In contrast, MHC class II promoters do not display enhancer A nor ISRE elements (Van den Elsen, P. J. et al, 1998, *Immunogenetics*. 48:208-221). Furthermore, RFX and CIITA in MHC class II gene regulation have been found of crucial importance as illustrated by studies with cell lines established from patients with the bare lymphocyte syndrome (BLS), a severe combined immunodeficiency due to mutations in one of the RFX subunits or CIITA (DeSandro, A. et al., 1999, *Am J Hum Genet*, 65:279-286). Also, lack of either CIITA or one of the RFX subunits affects the functioning and assembly of the MHC enhanceosome, respectively, leading to a lack of MHC class II and reduced levels of MHC class I transcription (Van den Elsen, P. J. et al. 2004, *Current Opinion in Immunology*, 16:67-75).

In one embodiment, the invention encompasses a method comprising inserting an MHC class I promoter into a lentiviral vector to direct expression of a transgene, which preferably encodes an immunogenic polypeptide, most preferably encoding a microbial antigen or therapeutic protein. The method can further comprise inserting any of the other nucleic acid elements mentioned herein, such as a DNA flap sequence.

Production of Lentiviral Particle Vectors

The present invention provides a method for producing a lentiviral particle vector, which preferably does not comprise enhancer sequences, but instead contains a class I MHC promoter. A lentiviral particle vector (or lentiviral vector particle) comprises a lentiviral vector in association with viral proteins. The vector can be integrative or non-integrative.

Replacing the viral enhancer sequences used in the prior art vectors to drive gene expression with a MHC class I promoter can improve the safety of retroviral vectors:

1) It reduces the risk of insertional mutagenesis linked to enhancer sequences; and 2) a MHC class I promoters are activated in most human cell types, if not all of them, so that, once the immune response is elicited against the product of the transgene, all the cells where the vector was integrated, whatever the cell-type, are eliminated by the immune system. Thus, after a period of time, the human body may not contain any replicates of such vector.

According to one embodiment of this method, the particle vector is obtained in a host cell transformed with a DNA plasmid.

Such a DNA plasmid can comprise:
bacterial origin of replication (ex: pUC ori);
antibiotic resistance gene (ex: KanR) for selection; and more particularly:
a lentiviral vector comprising at least one transgene transcriptionally linked to a MHC class I promoter.

Such a method allows producing a recombinant vector particle according to the invention, comprising the following steps of:

i) transfecting a suitable host cell with a lentiviral vector;

ii) transfecting said host cell with a packaging plasmid vector, containing viral DNA sequences encoding at least structural and polymerase (+/− integrase) activities of a retrovirus (preferably lentivirus); Such packaging plasmids are described in the art (Dull et al., 1998, *J Virol*, 72(11):8463-71; Zufferey et al., 1998, *J Virol* 72(12):9873-80).

iii) culturing said transfected host cell in order to obtain expression and packaging of said lentiviral vector into lentiviral vector particles; and iv) harvesting the lentiviral vector particles resulting from the expression and packaging of step iii) in said cultured host cells.

For different reasons, it may be helpful to pseudotype the obtained retroviral particles, i.e. to add or replace specific particle envelope proteins. For instance, this may be advantageous to have different envelope proteins in order to distinguish the recombinant particle from natural particles or from other recombinant particles. In matter of vaccination strategy, pseudotyped particle vectors are more likely to escape the immune system, when this latter already developed immunity against lentiviruses. This is particularly helpful when successive injections of similar particle vectors are required for immunizing a patient against a disease.

In order to pseudotype the retroviral particles of the invention, the host cell can be further transfected with one or several envelope DNA plasmid(s) encoding viral envelope protein(s), preferably a VSV-G envelope protein.

An appropriate host cell is preferably a human cultured cell line as, for example, a HEK cell line.

Alternatively, the method for producing the vector particle is carried out in a host cell, which genome has been stably transformed with one or more of the following components: a lentiviral vector DNA sequence, the packaging genes, and the envelope gene. Such a DNA sequence may be regarded as being similar to a proviral vector according to the invention, comprising an additional promoter to allow the transcription of the vector sequence and improve the particle production rate.

In a preferred embodiment, the host cell is further modified to be able to produce viral particle in a culture medium in a continuous manner, without the entire cells swelling or dying. One may refer to Strang et al., 2005, *J Virol* 79(3):1165-71; Relander et al., 2005, *Mol Ther* 11(3):452-9; Stewart et al., 2009, *Gene Ther*, 16(6):805-14; and Stuart et al., 2011, *Hum gene Ther* (in press), with respect to such techniques for producing viral particles.

An object of the present invention consists of a host cell transformed with a lentiviral particle vector.

The lentiviral particle vectors can comprise the following elements, as previously defined:
cPPT/CTS polynucleotide sequence; and
a transgene sequence under control of an MHC class I promoter, and optionally one of the additional elements described above.

Methods for Expressing a Transgene in a Cell

The present invention encompasses methods for expressing a transgene in a cell, preferably a non-dividing cell. The method comprises transducing a cell with a lentiviral vector or lentiviral particle vector of the invention under conditions that allow the expression of the transgene.

The cells are preferably mammalian cells, particularly human cells. Particularly preferred are human non-dividing cells.

The transgene preferably encodes an immunogenic polypeptide. The method can further comprise harvesting or isolating the polypeptide.

The lentiviral vector or lentiviral particle vector preferably comprises a class I MHC promoter.

In one embodiment, the invention encompasses a method for expressing a transgene comprising inserting an MHC class I promoter into a lentiviral vector such that it direct the expression of a transgene and transducing a cell with the vector containing the MHC class I promoter.

Therapeutic Use of Lentiviral Vectors

The present invention further relates to the use of the lentiviral vectors according to the invention, especially in the form of lentiviral particle vectors, for the preparation of therapeutic compositions or vaccines which are capable of inducing or contributing to the occurrence or improvement of an immunogical reaction against epitopes, more particularly those encoded by the transgene present in the vectors under the transcriptional control of the MHC class I promoter.

The present invention thus provides vectors that are useful as a medicament or vaccine.

These vectors are preferentially used for the treatment or prophylaxis of infectious diseases, especially diseases associated with virus infection and more particularly, with retrovirus infection, such as AIDS and other immunodeficiencies.

The invention can also be used in treatment protocols against tumors and cancers and especially could be used in protocols for immunotherapy or vaccination therapy against tumors.

As the vectors of the invention more specifically target dendritic cells to obtain a cell-mediated immune response and especially the CTL response associated with the antigen expressed by the transgene in these cells, they are particularly useful as vaccines targeting slow or endogenous pathogenic microorganisms such as Mycobacteria or HIV virus.

Accordingly, the invention relates to an immunogenic composition comprising a lentiviral vector as previously defined.

The immunogenic compositions of the invention preferably contain cPPT and CTS sequences in the vector and vector particles to induce or to stimulate the nuclear import of the vector genome in the target cells.

During reverse transcription, cPPT and CTS sequences induce the formation of a three stranded DNA structure referred as DNA triplex, which stimulates the nuclear import of DNA vector sequence. Preferably, the vector comprises a transgene and regulatory signals of retrotranscription, expression and encapsidation of retroviral or retroviral-like origin, wherein the composition is capable of inducing or of stimulating a CTL (Cytotoxic T Lymphocytes) and/or a CD4 response against one or several epitopes encoded by the transgene sequence present in the vector.

The expression of the transgene is greatly improved by inclusion of an MHC class I promoter in the vector.

Thus, the lentiviral vectors according to the invention have the ability to induce, improve, or in general be associated with the occurrence of a memory CTL response. In other words, they can be used for the preparation of therapeutic composition for the treatment of allergies, autoimmune diseases, tumor diseases, or infectious diseases, by induction of, stimulation of, or participation in the occurrence of a cell-mediated immune response, especially a CTL response or a memory response.

The lentiviral vectors of the invention can be used in methods of treatment and methods of inducing an immune response comprising administering the lentiviral vector to a host and generating a specific immune response against the transgene in the host. The cells and antibodies generated in these hosts can be used as diagnostic reagents.

The lentiviral vectors according to the invention can be directly administered to a patient through known routes of administration, including systemic, local, or cutaneous, intradermal, for instance intratumoral, administration routes. Ex vivo administration, for instance ex vivo transduction of target cells followed by administration of the treated cells to the patient to be treated, is also encompassed by the invention.

In a particular embodiment, the immunogenic composition according to the invention can be directly administered to the patient, in such a way that it will induce, improve, or participate in vivo in the occurrence of a cell-mediated immune response, especially a CTL-mediated immune response.

In another embodiment, the immunogenic compositions are used once or upon repeated administration so that they can enable the occurrence of a long-term memory cell mediated response.

A particular advantage of the immunogenic compositions of the invention is that they can be used to elicit or stimulate a cell-mediated immune response against multiple epitopes encoded by the nucleotides sequence of interest or transgene present in the vector or vector particles, and they can also be used to elicit or stimulate a cell-mediated immune response against the product of the entire sequence of a gene, for instance a gene of a pathogenic agent or fragments of said gene capable to encode at least 8 to 15 amino acids preferably 9 to 12 amino acids.

The invention also encompasses a lentiviral vector comprising a nucleotide sequence encoding a multiple repeat (at least 2 identical sequences) of said amino acid sequence inducing a cellular response and/or an amino acid sequence containing at least 2 different sequences corresponding to 2 epitopes of different pathogens or tumoral antigens.

As a result, the invention encompasses a composition that could be used in prophylactic and/or therapeutic vaccination protocols, for the treatment of tumors and especially as anti-cancer or anti-infectious diseases treatment.

In particular, it can be used in combination with adjuvants, other immunogenic compositions, chemotherapy, or any other therapeutic treatment.

Having thus described different embodiments of the present invention, it should be noted by those skilled in the art that the disclosures herein are exemplary only and that various other alternatives, adaptations, and modifications may be made within the scope of the present invention. Accordingly, the present invention is not limited to the specific embodiments as illustrated herein.

EXAMPLES

Example 1

GFP Expression Driven by Various Promoters in Two Different Cell Types

Lentivector constructions encompassing various promoters were used to transduce HEK293T (a fibroblastcell line) and BDCM (a dendritic-like cell line) cells, and the promoters' ability to drive the GFP expression was evaluated by flow cytometry. MFI (Mean Fluorescence intensity) in BDCM cells are represented in % of the MR obtained in 293T cells.

Viral (CMV) and ubiquitous (UBC and EF1α) promoters appear to be repressed in BDCM, while MHC I (HLA-A2, HLA-B7 and HLA-E) and MHC II (HLA-DRα) promoters are overexpressed in this cell type. The β2m promoter was also overexpressed in this cell type.

Cells were seeded in 24-well plates at a density of $1\times10^5$ cells per well in complete medium containing 10% FBS. For each cell types, 3 wells of $1\times10^5$ cells were transduced by replacing the culture medium with 300 µl of the dilution of viral samples which allowed a percentage of transduced cells included between 5 and 30%. The cells were then incubated 2 h at 37° C., 5% $CO_2$ and 1 ml of complete medium was added per well. 72 h post transduction, the cells were trypsinized and resuspended, and the GFP MFI was measured with a FACScalibur flow cytometer, using the FL1 channel.

Example 2

Induction of GFP Expression by Various Interferons

Lentivector encompassing various promoters were used to transduce HEK293T and BDCM cells in presence of various interferon molecules. The promoters' ability to drive the GFP expression was then evaluated. Reduced versions of the MHC-1 and β2m promoters were also tested, the HLA-A2-, HLA-B7-, HLA-E- and β2m-SXY promoters (promoters in which the κB and ISRE regulatory sequences were removed, transforming them into a MHCII like promoters).

As shown in FIG. 3, The MHCII promoter was not inducible by interferons in either 293 T or BDCM cells. However, the MHCI promoters were inducible by interferon γ in both cell types and by interferon α in 293 T cells. Similar to the MHCI promoters, the β2m promoter was also inducible by interferons. Truncation of the MHCI or β2m promoters to remove the ISRE and the NF-Kb binding sites (promoter-SXY-GFP), reduced inducibility. Thus, the truncated version of the HLA-A2, HLA-B7, HLA-E, and β2m promoters behave like a MHCII promoter with respect to inducibility.

Cells were seeded in 24-well plates at a density of $1\times10^5$ cells per well in complete medium containing 10% FBS. For each cell types, 12 wells of $1\times10^5$ cells were transduced by replacing the culture medium with 300 µl of the dilution of viral samples which allowed a percentage of transduced cells included between 5 and 30%. The cells were then incubated 2 h at 37° C., 5% $CO_2$ and 1 ml of complete medium was added to 3 wells, 1 ml of complete medium containing 650 U/mL (500 U final) of IFNγ was added to 3 other wells, 1 ml of complete medium containing 650 U/mL (500 U final) of IFNα was added to 3 other wells and 1 ml of complete medium containing 650 U/ml (500 U final) of IFNβ was added to the 3 last wells, for each vector transduction. Plates were then incubated at 37° C., 5% $CO_2$. At 72 h posttransduction, the cells were trypsinized and resuspended, and the GFP MFI was measured with a FACScalibur flow cytometer, using the FL1 channel.

Example 3

T-Specific Response (Median) in C57Bl/6j Mice

C57Bl/6j mice were immunized with $1\times10^6$TU of lentivectors in which a HIV antigen expression is driven by various promoters (viral, ubiquitous, MHCI and MHCII). 12 days after immunization, the specific T-cell responses were monitored in mice splenocytes by IFN-γ ELISPOT. As shown in FIG. 4, immunization with lentivectors encompassing a MHCI promoter give higher specific T-cell response than any other lentivectors used, even when a viral promoter is driving the antigen expression.

Splenocytes were isolated from the mice spleens immunized with lentivectors. 12 days after immunization and were used for the ELISPOT assays. Ninety-six-well tissue culture plates (Millipore) were coated overnight at 4° C. with 50 µl/well of 5 µg/ml anti-mouse IFNγ mAb (Mouse IFNγ Elispot pair; BD Biosciences Pharmingen). The plates were washed three times with 200 µl DPBS/well and blocked with 200 µl/well of DPBS/10% fetal bovine serum for 2 h at 37° C. The plates were washed three times with 200 µl DPBS/well. Splenocytes were added to the plates in triplicate at 2.5, 4.1, or $5.1\times10^5$ cells/well and stimulated with 2 µg/ml of stimulatory peptides (specific to the antigen), concanavalin A (5 µg/ml; source), or culture medium alone. The plates were incubated for 18 h at 37° C. and then rinsed three times with 200 µl/well of DPBS/0.05% Tween 20 and three times with 200 µl/well of DPBS. For detection, 50 µl/well of 2 µg/ml anti-mouse IFNγ-biotinylated monoclonal antibody (BD Pharmingen) were added for 2 h at room temperature. Plates were washed and 100 µl/well of streptavidin-alkaline phosphatase (Roche) diluted 1:2000 in Dulbecco's PBS for 90 min at room temperature. After washing the plates, spots (IFNγ-secreting cells) were visualized by adding 60 µl/well of BCIP/NBT solution (Sigma). Plates were incubated for 15-30 min at room temperature until blue spots developed and then thoroughly washed with running tap water and air-dried for 24 h. Finally, the spots were counted using a Bioreader 2000 (Biosys).

---

We claim:

1. A lentiviral vector comprising a transgene sequence encoding an immunogenic polypeptide, wherein the transgene sequence is under the transcriptional control of a MHC class I promoter.

2. The lentiviral vector of claim 1, wherein the vector induces a greater CTL response in vivo against the encoded immunogenic polypeptide than a vector in which the transgene sequence is under the transcriptional control of a CMV promoter.

3. The lentiviral vector of claim 1, comprising a cPPT/CTS sequence from a lentivirus.

4. The lentiviral vector of claim 3, wherein the MHC class I promoter is an HLA-A2 promoter.

5. The lentiviral vector of claim 3, wherein the MHC class I promoter is an HLA-B7 promoter.

6. The lentiviral vector of claim 3, wherein the MHC class I promoter is an HLA-Cw5 promoter.

7. The lentiviral vector of claim 3, wherein the MHC class I promoter is an HLA-F promoter.

8. The lentiviral vector of claim 3, wherein the MHC class I promoter is an HLA-E promoter.

9. The lentiviral vector of claim 3, wherein said promoter sequence comprises a polynucleotide sequence that shares more than 95% identity with the promoter sequence of SEQ ID NO:1, SEQ ID NO:2, SEQ ID NO:3, SEQ ID NO:4, or SEQ ID NO:5.

10. The lentiviral vector of claim 3, comprising an LTR that is deleted for the promoter and enhancer of U3.

11. The lentiviral vector of claim 10, wherein the lentiviral vector does not contain an enhancer.

12. The lentiviral vector of claim 3, wherein said immunogenic polypeptide comprises antigen(s) from Gag, Pol or Nef proteins from an HIV virus or at least one tumour antigen.

13. An isolated host cell comprising the lentiviral vector of claim 1.

14. A method for producing a lentiviral vector particle comprising the steps of:
   a) transfecting a suitable host cell with the lentiviral vector of claim 1;
   b) transfecting said host cell with a packaging plasmid vector containing viral DNA sequences encoding at least structural and polymerase activities of a retrovirus;
   c) culturing said transfected host cell in order to obtain expression and packaging of said lentiviral vector into lentiviral vector particles; and
   d) harvesting the lentiviral vector particles resulting from the expression and packaging of step c) in said cultured host cells.

15. A lentiviral vector particle comprising the lentiviral vector of claim 1.

16. A lentiviral vector particle comprising at least the following sequence elements:
   a) cPPT/CTS polynucleotide sequence;
   b) an LTR sequence that is deleted for the promoter and enhancer of U3; and
   c) a transgene sequence under control of an MHC class I promoter.

17. The lentiviral vector particle of claim 12, wherein said promoter sequence comprises a polynucleotide sequence that shares more than 95% identity with the promoter sequence of SEQ ID NO:1, SEQ ID NO:2, SEQ ID NO:3, SEQ ID NO:4, or SEQ ID NO:5.

18. A method for inducing a T-cell response comprising administering to a patient a lentiviral vector particle of claim 15.

19. The method of claim 18, wherein the lentiviral vector particle comprises a cPPT/CTS polynucleotide sequence; an LTR that is deleted for the promoter and enhancer of U3; and a transgene sequence under control of an MHC class I promoter.

* * * * *